United States Patent [19]

Beuther et al.

[11] 4,413,064

[45] Nov. 1, 1983

[54] FLUID BED CATALYST FOR SYNTHESIS GAS CONVERSION AND UTILIZATION THEREOF FOR PREPARATION OF DIESEL FUEL

[75] Inventors: Harold Beuther, Cheswick; Charles L. Kibby, Gibsonia; T. P. Kobylinski, Prospect; Richard B. Pannell, Allison Park, all of Pa.

[73] Assignee: Gulf Research & Development Company, Pittsburgh, Pa.

[21] Appl. No.: 310,977

[22] Filed: Oct. 13, 1981

[51] Int. Cl.$^3$ ............................................... C07C 1/04
[52] U.S. Cl. ....................................... 518/715; 44/50
[58] Field of Search ............................ 518/715; 44/50

[56] References Cited

U.S. PATENT DOCUMENTS

| 3,536,632 | 6/1970 | Kroll | 252/430 |
|---|---|---|---|
| 4,073,750 | 7/1978 | Yates et al. | 252/459 |
| 4,088,671 | 5/1978 | Kobylinski | 518/715 |
| 4,142,962 | 5/1979 | Yates et al. | 208/109 |
| 4,192,777 | 11/1980 | McVicker et al. | 252/447 |

OTHER PUBLICATIONS

Twentieth Annual Spring Symposium of The Pittsburgh Catalysis Society, Program and Abstracts, May 27–29, 1981, Marriott Hotel, Monroeville, Pa.

*Primary Examiner*—Howard T. Mars
*Attorney, Agent, or Firm*—Deane E. Keith; Forrest D. Stine; Donald L. Rose

[57] ABSTRACT

A catalyst useful in the conversion of synthesis gas to diesel fuel in a fluidized bed is prepared by contacting finely divided alumina with an aqueous impregnation solution of a cobalt salt, drying the impregnated support and thereafter contacting the support with a nonaqueous, organic impregnation solution of salts of ruthenium and a Group IIIB or IVB metal.

17 Claims, No Drawings

FLUID BED CATALYST FOR SYNTHESIS GAS CONVERSION AND UTILIZATION THEREOF FOR PREPARATION OF DIESEL FUEL

REFERENCES TO RELATED APPLICATIONS

U.S. Ser. No. 310,969, filed Oct. 13, 1981 entitled "CONVERSION OF SYNTHESIS GAS TO DIESEL FUEL AND CATALYST THEREFOR" to Harold Beuther, T. P. Kobylinski, Charles L. Kibby and Richard B. Pannell.

U.S. Ser. No. 310,972, filed Oct. 13, 1981 entitled "PROCESS FOR PREPARING GASOLINE RANGE HYDROCARBONS FROM SYNTHESIS GAS AND CATALYST USED THEREFOR" to Harold Beuther, T. P. Kobylinski, Charles L. Kibby and Richard B. Pannell.

U.S. Ser. No. 310,973, filed Oct. 13, 1981 entitled "CONVERSION OF SYNTHESIS GAS TO DIESEL OIL AND GASOLINE" to Harold Beuther, T. P. Kobylinski, Charles L. Kibby and Richard B. Pannell.

which are hereby incorporated by reference.

FIELD OF THE INVENTION

This invention relates to a fluid bed catalyst, its preparation and to the use of such catalyst for the conversion of synthesis gas to paraffins boiling in the diesel fuel range. More particularly, this invention relates to the preparation of a highly active catalyst comprising cobalt, ruthenium, thoria or lanthana on an alumina support, and to the use of such catalyst for the conversion of synthesis gas to diesel fuel in a fluidized bed.

BACKGROUND OF THE INVENTION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons of the catalyzed reaction of CO and hydrogen. Commercial plants have operated in Germany, South Africa and other parts of the world based on the use of particular catalysts. The German commercial operation, for example, concentrated on the use of a precipitated cobalt-thoria-kieselguhr fixed-bed catalyst, and a later modification where MgO, for economy reasons, replaced part of the thoria.

Co-pending U.S. application Ser. No. 310,969 filed Oct. 13, 1981 entitled "Conversion of Synthesis Gas to Diesel Fuel and Catalyst Therefore" to H. E. Beuther, C. L. Kibby, T. P. Kobylinski and R. B. Pannell, which is hereby incorporated by reference, discloses a catalyst containing cobalt and a Group IIIB or IVB metal oxide supported on gamma and/or eta alumina for the conversion of synthesis gas to diesel fuel in which the catalyst is produced by using a nonaqueous, organic solvent impregnation solution. The procedure described therein produced very active catalyst. However, when high cobalt loadings are utilized, there is a tendency for the support particles to agglomerate, which could provide problems when using the catalyst in a fluidized bed.

SUMMARY OF THE INVENTION

It has now been found in accordance with the present invention, that a highly active catalyst for the conversion of synthesis gas consisting essentially of CO and hydrogen to a product high in straight chain paraffins in the diesel fuel boiling range ($C_9$–$C_{21}$) can be produced using a two-step impregnation technique which consists essentially of contacting finely divided alumina with (A) an aqueous impregnation solution of a cobalt salt, and (B) a nonaqueous, organic impregnation solution of a ruthenium salt and a salt of a Group IIIB or IVB metal oxide. Surprisingly, it was found that by initially impregnating the finely divided alumina support with an aqueous impregnation solution of a cobalt salt, drying the impregnated support, and thereafter impregnating the support with a nonaqueous organic solvent impregnation solution with salts of ruthenium and a Group III or Group IV metal oxide, the resulting catalyst was highly active and selective for the production of $C_5+$ liquid hydrocarbons including naphtha and diesel fuel, while avoiding the agglomeration problems encountered using a nonaqueous organic solvent impregnation solution, thereby resulting in a catalyst especially useful in a fluidized bed. The catalysts of the present invention have high activity, good selectivity to liquids, proper particle size distribution, and a high attrition resistance necessary for hydrocarbon liquid synthesis in a fluidized bed reactor.

DESCRIPTION OF THE PREFERRED EMBODIMENTS

The preferred catalyst of the present invention consists essentially of cobalt, ruthenium, and a Group IIIB or Group IVB metal oxide on an alumina support.

In accordance with the process of the present invention, the cobalt component is deposited onto the finely divided alumina support by means of an aqueous solution of a soluble cobalt salt. Suitable cobalt salts include, for example, cobalt nitrate, cobalt acetate, cobalt acetylacetonate or the like with cobalt nitrate being especially preferred.

The alumina support of the present invention is preferably either gamma-alumina or eta-alumina or mixtures thereof characterized as having low acidity, a high surface area and high purity. The expression "low acidity" as used in the present application means that the alumina support has a Brϕnsted activity with $H_o \leq 1.5$ which is less than 5 micromol per gram or about $10^{16}$ acid sites per square meter of surface area. The low acidity of the support is required in order to enable the catalyst to provide a high molecular weight hydrocarbon product boiling in the diesel fuel range.

The catalyst of the present invention has a hydrogen chemisorption value of at least 100, preferably from about 125 to about 300 especially 150 or 200 up to 300 micromol hydrogen per gram of total catalyst when measured at 25° C., which values are substantially higher than achieved using an aqueous impregnation solution containing similar metals.

The surface area of the alumina support of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram. As indicated, the catalyst support of the present invention must be of high purity. The expression "high purity" as used in the present application means that the catalyst contains negligible amounts of sodium, sulphate, silicon, phosphates or other material having a deleterious effect on the metal dispersion or the production of high molecular weight hydrocarbon products. For impurities creating acid sites, less than 5 micromol per gram should be present (about 0.01–0.1 weight percent depending on molecular weight). The deleterious effect of acidity is isomerization and cracking of intermediate olefins, removing them from chain growth and producing a low molecular weight product.

Any suitable impregnation technique can be employed for depositing the cobalt onto the alumina support including techniques well known to those skilled in the art so as to distend the cobalt in a uniform thin layer on the catalyst support. For example the cobalt can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess aqueous solvent is merely removed by evaporation. Thus, the impregnation solution can be added in excess, namely, up to five times the pore volume of the alumina, or can be added using just enough solution to fill the pore volume of the alumina.

Next the impregnation solution and alumina are stirred while evaporating the aqueous solvent at a temperature of from about 25° to about 120° C. until "dryness".

Next, the cobalt-impregnated alumina is further impregnated with a nonaqueous, organic impregnation solution consisting essentially of a soluble ruthenium salt and a soluble Group IIIB or IVB salt.

Any suitable ruthenium salt can be employed including the nitrates, chlorides and acetates, especially ruthenium acetylacetonate.

Likewise, any suitable Group IIIB or Group IVB metal salt, such as thorium nitrate, thorium acetate or the like can be employed. In general, any metal salt which is soluble in the organic solvent of the present invention and will not introduce any significant acidity or have a significant poisonous effect, e.g. a halide, on the catalyst can be utilized. Thorium nitrate is especially preferred.

A nonaqueous organic solvent solution of the Group III or Group IV salt is prepared. The nonaqueous organic solvent of the present invention is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents include, for example, ketones, such as acetone, butanone (methyl ethyl ketone); the lower alcohols, e.g., methanol, ethanol, propanol and the like; amides, such as dimethyl formamide: amines, such as butylamine; ethers, such as diethylether; hydrocarbons, such as pentane and hexane; and mixtures of the foregoing solvents.

The preferred solvent of the present invention is a mixture of ethanol and acetone, for example, in a weight ratio of about four parts acetone per part of ethanol.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

As in the case of the aqueous impregnation step, any suitable impregnation technique including the "incipient wetness technique" or the excess solution technique can be employed for depositing the nonaqueous organic solvent solution onto the alumina support.

Next, the impregnation solution and alumina are stirred while evaporating the solvent at a temperature of from about 25° to about 45° C. until solvent "dryness". The impregnated catalyst is then oven dried at a temperature of from about 100° to about 120° C. for a time sufficient, e.g., 12 to about 24 hours to substantially remove the water of hydration of the salt.

If additional impregnations are needed to obtain the desired metal loading, for example, when the incipient wetness technique is used, the dried catalyst is then calcined in the presence of an oxygen-containing or inert, e.g. nitrogen, gas at a temperature just sufficient to decompose the metal salts and fix the cobalt. Suitable calcination temperatures include those in the range of from about 150° to about 300° C., preferably from about 225° to about 275° C. Such impregnation, drying and calcination can be repeated until the desired metal loading is achieved.

After the last impregnation sequence, the impregnated catalyst is preferably slowly reduced in the presence of hydrogen at a temperature from about 250° C. to about 400° C. overnight. Although pure hydrogen can be employed for this reduction step, a mixture of hydrogen and nitrogen can be utilized in order to slowly reduce the catalyst. For example, the reduction step can be conducted initially using a gaseous mixture comprising 5% hydrogen and 95% nitrogen, and thereafter, the concentration of hydrogen can be gradually increased until pure hydrogen is obtained so as to slowly reduce the catalyst. Such slow reduction is particularly desirable when the metal salts utilized in the impregnation step are nitrates so as to avoid the dangers involved with an exothermic reaction in which nitrates are given off. Thus, the slow reduction may involve the use of a mixture of hydrogen and nitrogen at 100° C. for about one hour; increasing the temperature 0.5° C. per minute until a temperature of 200° C.; holding that temperature for approximately 2 hours; and then increasing the temperature 1° C. per minute until a temperature of 350° C. is reached and then continuing the reduction for approximately 16 hours. Such slow reduction process is not required when the cobalt salt is not a nitrate, e.g. cobalt acetate.

It is preferred to omit the calcination step following the last impregnation and subject the impregnated catalyst directly to the slow reduction process.

The fluid catalyst of the present invention is microspheroidal and has an average particle diameter of from about 0.02 to about 0.15 millimeter, preferably from about 40 to about 80 microns, with a broad distribution of particles such that from about 15 to 35 weight percent of the particles have a diameter below 40 microns; about 40 to 60 weight percent are between 40 and 80 microns; and about 15 to 35 weight percent are between 80 and 150 microns.

The resulting catalyst thus contains cobalt, ruthenium and a Group IIIB or IVB metal oxide.

Any suitable Group IIIB or IVB metal oxide can be employed in the catalyst of the present invention, with oxides of the actinides and lanthanides being preferred. Thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lu_2O_3$, $UO_2$, $UO_3$, $U_3O_8$, $UO_4.2H_2O$, and the like. Especially preferred metal oxides for inclusion in the catalyst of the present invention include $ThO_2$, $La_2O_3$, $CeO_2$, $ZrO_2$, $TiO_2$, $HfO_2$, and unseparated rare earth oxide mixtures high in lanthanum, praseodynium, and neodynium. The most preferred metal oxide for use in the catalyst of the present invention is thoria and reference will be hereinafter made thereto for example.

Thus, the catalyst of the present invention can contain the Group IIIB or IVB metal oxide, e.g. thoria, in amounts of from 0 or about 0.05 to about 100 parts by weight per 100 parts by weight cobalt, preferably from about 0.5 to 25 parts per 100 parts cobalt, with from about 1 to about 10 parts by weight per 100 parts by weight cobalt being especially preferred. The relatively low levels of the Group IIIB or IVB metal oxide control residual catalyst impurities. Thus, such component can be omitted and the catalyst is still operative. In order to omit the Group IIIB or IVB metal oxide from the catalyst, it is merely omitted from the impregnation solution.

Ruthenium is present in amount of from about 0.1 to about 50 parts by weight, preferably from about 1 to about 10 parts by weight, especially from about 2 to about 5 parts by weight, per 100 parts by weight cobalt.

The alumina support which is composed of gamma-alumina, eta-alumina or mixtures thereof is present in an amount of from about 10 to about 10,000 parts by weight alumina per 100 parts by weight of cobalt, preferably between about 100 and about 2,000 parts of alumina per 100 parts of cobalt, with from about 200 to about 400 parts by weight of alumina per 100 parts by weight cobalt being especially preferred. Pure gamma-alumina is preferred.

The charge stock used in the process of this invention is a mixture of CO and hydrogen. The source of the CO and hydrogen to be used in the charge stocks for this invention is not critical and can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed.

The molar ratio of hydrogen to CO in the charge stock can be, for example, from about 0.5:1 to about 4:1 or higher, e.g., 10:1, preferably, from about 1:1 to about 2.5:1, with 1.5:1 to about 2:1 being especially preferred.

The reaction temperature is suitably from about 160° to about 350° C., preferably from about 175° to about 250° C., and most preferably from about 185° to about 215° C. The total pressure is from about 1 to about 100 atmospheres, preferably from about 1 to about 50 atmospheres, and most preferably from about 1 to about 20 atmospheres. The hydrogen partial pressure is from about 0.5 to about 30 atmospheres, preferably from about 0.5 to about 25 atmospheres, and most preferably from about 1 to about 20 atmospheres.

The gaseous hourly space velocity based upon the total amount of feed is less than 20,000 volumes of gas per volume of catalyst per hour, preferably from about 100 to about 5,000 v/v/hour, with from about 200 to about 2,500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The invention will be further described with reference to the following experimental work:

EXAMPLE 1

A catalyst was made by impregnating pure microspheroidal gamma-alumina (commercially available from Harshaw) having an average particle diameter of about 60 microns and calcined for two hours at 600° C., with cobalt nitrate $[Co(NO_3)_2.6H_2O]$ dissolved in water using one milliliter of the nitrate per gram of support. Next, the impregnated support was dried at 120° C. for 16 hours. It was then impregnated with thorium nitrate $[Th(NO_3)_4.4H_2O]$ and ruthenium acetylacetonate dissolved in an acetone-ethanol solution in a ratio of acetone/ethanol of approximately 2:1. The amount of solvent was 2 milliliters per gram of alumina. Excess solvent was removed by evaporation at a reduced pressure of approximately 0.01 atmosphere and 25°–30° C. in a rotary evaporator. The catalysts were dried at a temperature of 90° C. with moderate stirring. Melting of the nitrate salt and evolution of water occurred at approximately 50°–60° C. After the water had evolved, the catalyst appeared to be dry.

Prereduction and passivation of the impregnated catalyst was conducted using pure hydrogen at the rate of 720 cm$^3$/gram/hour. The impregnated catalyst was heated to 100° C. at the rate of 1° C. per minute and then maintained at that temperature for about one hour. Next, the catalyst was heated at the rate of 1° C. per minute to a temperature of 200° C. and then held at 200° C. for approximately two hours. The catalyst was then heated at the rate of 10° C. per minute until a temperature of 360° C. was reached and then held at that temperature for sixteen hours. Next, the catalyst was cooled to below 200° C., purged with nitrogen and further cooled. Air was bled into the nitrogen flow at approximately 1 cubic centimeter of air in 50 cubic centimeters of nitrogen per minute per 5 grams of catalyst for a period of sixteen hours.

The final composition of the reduced catalyst was 21.9 weight percent cobalt, 0.5 weight percent ruthenium, 2.2 weight percent $ThO_2$ and 75.4 weight percent alumina.

EXAMPLES 2–6

A run was conducted using the catalyst of Example 1 in a ½ inch I.D. fluid bed reactor wherein a 50 gram sample of the catalyst was initially heated to a temperature of 350° C. in hydrogen flowing at the rate of about 1000 cm$^3$/gram/hour and then held overnight.

The hydrogen flow was then reduced to 300–400 cm$^3$/gram/hour and an equal flow of carbon monoxide was initiated. For those runs where the molar ratio of hydrogen/CO is 2:1, the hydrogen flow rate was increased to double.

Sampling was conducted periodically to analyze the products. The conditions utilized in each run and the product distribution is set forth in Table I:

TABLE I

| Ex. No. | 2 | 3 | 4 | 5 | 6 |
|---|---|---|---|---|---|
| Temp., °C. | 195 | 195 | 195 | 205 | 215 |
| Pressure, psia | 15 | 15 | 30 | 30 | 30 |
| $H_2/CO$ | 1:1 | 2:1 | 2:1 | 2:1 | 2:1 |
| CO Flowrate ($cm^3$/gram/hour) | 310 | 310 | 735 | 735 | 735 |
| CO Conversion Rate ($cm^3$/gram/hour) | 70 | 95 | 102 | 200 | 257 |
| $C_5+$ Synthesis Rate (mg./gram/hour) | 38 | 48 | 47 | 83 | 97 |
| Product Distribution (Carbon Atom %) | | | | | |
| $CH_4$ | 6 | 10 | 15 | 19 | 22 |
| $C_5$ | 88 | 79 | 73 | 64 | 58 |
| $C_9-C_{20}$ | 57 | 45 | 41 | 32 | 25 |
| $C_{21}+$ | 9 | 5 | 6 | 4 | 1 |
| $CO_2$ | 2 | 2 | 1 | 2 | 2 |

As seen in Table I, as the temperature is increased from 195° C. to 215° C. the CO conversion rate increases. The selectivities to $C_9-C_{20}$ range product are approximately 41–57% at 195° C. at conversion rates of 70 to 100 $cm^3$/gram/hour. The foregoing indicates both high activity and selectivity to diesel fuel.

EXAMPLE 7

The procedure of Example 1 was repeated with exception that lanthanum nitrate hexahydrate was substituted for the thorium nitrate tetrahydrate in an amount so as to provide 10 weight percent lanthanum oxide in the reduced catalyst.

When tested in a fixed bed microreactor it had substantially the same activity and selectivity as did the catalyst of Example 1.

EXAMPLE 8

The procedure of Example 7 was repeated with the exception that the final reduced catalyst contained one weight percent lanthanum and, in addition, magnesium nitrate was added along with the lanthanum salt to the impregnation solution to provide one percent magnesium oxide in the final, reduced catalyst.

The activity of this catalyst was 20 percent lower than the catalyst of Example 7, and the selectivity to liquid hydrocarbons was about 10 percent lower than the Example 7 catalyst.

EXAMPLE 9

A catalyst was prepared having a composition identical to that of Example 1, using a one-step impregnation in the manner of the organic solvent impregnation step of Example 1 in which the cobalt nitrate was also dissolved in the organic solvent. Three milliliters of organic solvent per gram of alumina were used.

This catalyst was tested in a fixed bed reactor and had essentially the same activity and selectivity of that of the catalyst of Example 1. However, the catalyst particles were agglomerated into particles which were too large to be fluidizable in the manner of the catalyst of Example 1.

What is claimed is:

1. A process for the conversion of synthesis gas to a product high in straight chain paraffins in the diesel fuel boiling range, which comprises contacting said synthesis gas under conversion conditions with a catalyst consisting essentially of cobalt, thoria or lanthana and ruthenium on an alumina support wherein said alumina is gamma-alumina, eta-alumina or a mixture thereof, said catalyst prepared by contacting finely divided alumina with (A) an aqueous impregnation solution of a cobalt salt, and (B) a nonaqueous, organic impregnation solution of a ruthenium salt and a salt of thorium or lanthanum.

2. The process of claim 1 wherein said organic impregnation solution contains salts of ruthenium and thorium.

3. The process of claim 1 wherein said organic impregnation solution contains salts of ruthenium and lanthanum.

4. The process of claim 1 wherein said finely divided alumina has an average particle diameter in the range of from about 20 to about 80 microns.

5. The process of claim 1 wherein said synthesis conversion process is conducted in a fluidized bed.

6. The process of claim 1 wherein impregnation of the aqueous solution of the cobalt salt solution is conducted using the incipient wetness technique.

7. The process of claim 1 wherein the molar ratio of hydrogen to CO is from about 0.5:1 to about 4:1.

8. The process of claim 7 wherein the molar ratio of hydrogen to CO is from about 1:1 to about 2.5:1.

9. The process of claim 1 wherein the synthesis gas conversion conditions include a temperature of from about 160° to about 350° C.

10. The process of claim 9 wherein said temperature is from about 175° to about 250° C.

11. The process of claim 1 wherein the total pressure is from about 1 to about 50 atmospheres.

12. The process of claim 1 wherein said organic solvent comprises a lower alcohol.

13. The process of claim 1 wherein said solvent comprises acetone.

14. The process of claim 1 wherein said solvent has a relative volatility of at least 0.1.

15. The process of claim 1 wherein said salts are nitrates.

16. The process of claim 1 wherein the impregnated alumina support is dried prior to impregnation with the nonaqueous, organic solvent impregnation solution.

17. The process of claim 16 wherein said drying is conducted at a temperature of from about 25° to about 120° C.

* * * * *

UNITED STATES PATENT OFFICE
CERTIFICATE OF CORRECTION

Patent No. 4,413,064    Dated November 1, 1983

Inventor(s) Harold Beuther, Charles L. Kibby, T. P. Kobylinski, and Richard B. Pannell It is certified that error appears in the above-identified patent and that said Letters Patent are hereby corrected as shown below:

Col. 7, line 13, "$C_5$" should read --$C_5+$--.

Signed and Sealed this

Thirtieth Day of April 1985

[SEAL]

Attest:

DONALD J. QUIGG

Attesting Officer    Acting Commissioner of Patents and Trademarks